(12) United States Patent
Fitzpatrick et al.

(10) Patent No.: US 9,572,674 B2
(45) Date of Patent: Feb. 21, 2017

(54) PROSTHESIS

(75) Inventors: Noel Fitzpatrick, Godalming (GB);
Gordon Blunn, Godalming (GB);
Jayantilal Mohanlal Meswania,
Godalming (GB)

(73) Assignee: Fitzbionics Limited (GB)

( * ) Notice: Subject to any disclaimer, the term of this patent is extended or adjusted under 35 U.S.C. 154(b) by 0 days.

(21) Appl. No.: 14/128,673

(22) PCT Filed: Jun. 14, 2012

(86) PCT No.: PCT/GB2012/051364
§ 371 (c)(1),
(2), (4) Date: Jan. 23, 2014

(87) PCT Pub. No.: WO2012/175936
PCT Pub. Date: Dec. 27, 2012

(65) Prior Publication Data
US 2014/0148912 A1    May 29, 2014

(30) Foreign Application Priority Data

Jun. 23, 2011 (GB) .................................. 1110679.6

(51) Int. Cl.
*A61F 2/42* (2006.01)
*A61F 2/30* (2006.01)

(52) U.S. Cl.
CPC .... *A61F 2/4261* (2013.01); *A61F 2002/30703* (2013.01); *A61F 2002/4264* (2013.01); *A61F 2002/4269* (2013.01)

(58) Field of Classification Search
CPC ............ A61F 2/4261; A61F 2002/4264; A61F 2002/4266; A61F 2002/4269; A61F 2/42
See application file for complete search history.

(56) References Cited

U.S. PATENT DOCUMENTS

| 5,458,646 A | 10/1995 | Giachino |
| 5,853,413 A | 12/1998 | Carter et al. |
| 2009/0254189 A1* | 10/2009 | Scheker ............... A61F 2/4261 |
| | | 623/21.11 |

FOREIGN PATENT DOCUMENTS

| GB | 1 412 376 | 11/1975 |
| GB | 2 269 752 | 2/1994 |
| WO | 01/01892 | 1/2001 |

OTHER PUBLICATIONS

UK Search Report, GB Patent Application No. 1110679.6, dated Oct. 24, 2011.

(Continued)

*Primary Examiner* — Katrina Stransky
*Assistant Examiner* — Daniel Bissing
(74) *Attorney, Agent, or Firm* — Andrus Intellectual Property Law, LLP (57) ABSTRACT

A prosthesis for implantation in an animal or human subject, said prosthesis comprising a first component for attaching to a radius bone in use and a s second component for attaching to an ulna bone in use, the prosthesis further comprising a linkage for linking the first and second components substantially rigidly with respect to one another in use. Preferably the prosthesis is configured to allow the linkage to move relative to the first and/or second components and be retained substantially rigidly at a selected position in normal use, such that the first and second components can be retained substantially rigidly relative to one another in normal use.

25 Claims, 8 Drawing Sheets (56) References Cited

OTHER PUBLICATIONS

International Search Report, PCT/GB2012/051364, date of mailing Jul. 30, 2012.

* cited by examiner

PROSTHESIS

FIELD OF THE INVENTION

The invention relates to a prosthesis for implantation in an animal or human subject. The prosthesis may in particular be used for implantation at a joint, such as a carpal joint. The invention also relates to modular prosthesis kits and methods of installing prostheses.

BACKGROUND TO THE INVENTION

The problem of bone tumours in the human population has been well known for many years and a number of treatment options are available for dealing with this problem in humans, including limb salvage surgery, sometimes involving implantation of bone replacement implants. Bone cancers are common in dogs, often occurring at the distal part of the radius. However, although bone tumours such as osteosarcomas have been known about in the animal kingdom for many years, to date there is very little option except for amputation of the limb containing the bone tumour or euthanasia. Bone replacement implants that have been used in humans are not considered suitable for use in animals as animal joint loading patterns are different. For example, implants that are used in human upper limbs are not suitable for the forelimb of a dog, as the forelimbs are weight bearing. Furthermore, there can be little or no feedback from the animal subject.

There is a need for a cost effective treatment system for treating animals with bone tumours, in particular distal radial disease, and in particular distal radial disease in canines.

SUMMARY OF INVENTION

According to a first aspect of the invention there is provided a prosthesis for implantation in an animal or human subject, said prosthesis comprising a first component for attaching to a radius bone in use and a second component for attaching to an ulna bone in use, the prosthesis further comprising a linkage for linking the first and second components substantially rigidly with respect to one another in use.

The linkage can lock the first and second components together in a rigid configuration. When implanted, this locks the radius and ulna in a fixed configuration relative to one another. The inventor has realised that pronation and supination in the forelimb of an animal in which a radial replacement prosthesis is implanted and which has an absence of muscle attachment in this region is detrimental to the animal. A lack of such rigid fixation produces uncontrolled pronation and supination which hinders the animal from useful gait, causing great discomfort and pain in use of the limb. When implanted in a four legged animal such as a dog, the prosthesis of the present invention prevents the forelimb from pronating or supinating, thus providing a useful treatment for distal radial disease and other conditions. The present invention provides a radial replacement prosthesis for replacing at least part or all of a radius bone. As such, the invention provides massive bone replacement.

The present invention is useful not only for implantation in the forelimbs of four legged animals such as dogs, but also in humans where fixation of the radius relative to the ulna may be desirable in certain situations.

The present invention is particularly suitable for implantation at a subject's wrist joint. When implanted at a subject's wrist joint, the prosthesis of the present invention can be used to cause arthrodesis at the wrist joint.

Suitably, the first component is a radial component and the second component is an ulna component.

Preferably the prosthesis is configured to allow the linkage to move relative to the first and/or second components and be retained substantially rigidly at a selected position in normal use, such that the first and second components can be retained substantially rigidly relative to one another in normal use. In other words, the linkage is moveable relative to the first and/or second components to allow adjustment of the linkage relative to the first and/or second components, yet the linkage can also be configured to be retained substantially rigidly for normal use, once it has been adjusted to a selected position. This allows the linkage to be adjustable to provide a rigid fixation between the first and second components in normal use, irrespective of the relative orientations of a subject's radius and ulna.

Preferably the linkage provides at least two degrees of freedom of movement of the first component relative to the second component. The linkage can therefore provide rigid fixation of the radius relative to the ulna irrespective of their orientations by virtue of the multiple degrees of freedom of the first component relative to the second component due to the adjustable linkage. These may be rotational and/or translational degrees of freedom.

Preferably the linkage provides at least three degrees of freedom of movement of the first component relative to the second component.

Preferably the linkage provides at least four degrees of freedom of movement of the first component relative to the second component.

Preferably the linkage provides at least five degrees of freedom of movement of the first component relative to the second component.

Suitably the linkage has at least two degrees of freedom relative to the first component and at least two degrees of freedom relative to the second component. The linkage may comprise first and second parts which are moveable relative to one another to adjust the orientation of the first component relative to the second component, the two parts of the linkage having at least one degree of freedom of movement relative to one another.

Preferably the prosthesis further comprises a shaft extending from the first component in use, the linkage being rotatably coupleable to the shaft. Suitably the shaft has a longitudinal axis and the linkage is rotatable relative to that axis.

Preferably the linkage is translationally coupleable to the shaft.

Preferably the shaft is removably attachable to the first component. Alternatively the shaft may be integral with the first component.

Preferably the linkage comprises a shaft receiving member and a coupling member, the shaft receiving member receiving the shaft in use, the coupling member being coupled to the shaft receiving member and the second component in use.

Preferably the coupling member is pivotally coupleable to the shaft receiving member in use.

Preferably the linkage comprises a clevis ring, the clevis ring having a bore for receiving the shaft in use.

Preferably the linkage further comprises a clevis bolt, the clevis ring having first and second overlapping ears, said ears having channels therein for receiving said clevis bolt. Preferably said coupling member has a channel for receiving said clevis bolt, to fixedly couple the coupling member to the clevis ring in use. Suitably the coupling member can pivot relative to the shaft receiving member during adjustment; then by tightening the clevis bolt, the coupling member can be held rigidly relative to the shaft receiving member.

Preferably the coupling member has a longitudinal axis, the prosthesis further comprising fixing means for fixing the coupling member to the second component, the fixing means being configured to allow the second component to rotate relative to the longitudinal axis of the coupling member and be retained substantially rigidly at a selected position in normal use. The fixing means may also be configured to allow the second component to translate relative to the coupling member and be retained substantially rigidly at a selected position in normal use.

Preferably the fixing means comprises a bolt and corresponding cap, the cap and the second component having bores for receiving the bolt in use to secure the cap to the second component in use, such that the coupling member can be held between the second component and cap in use by friction engagement.

Preferably the coupling member comprises a rod and a cap, the cap having an elongate portion extending therefrom, the rod having a bore for receiving the elongate portion of the cap in use. Suitably the elongate portion can rotate relative to the rod and can be retained substantially rigidly at a selected position relative to the rod in normal use. Suitably the elongate portion may move translationally relative to the rod and can be retained substantially rigidly at a selected position relative to the rod in normal use.

Preferably the shaft receiving member is configured to receive said rod in use. Suitably the rod can rotate relative to the shaft receiving member and can be retained substantially rigidly at a selected position relative to the shaft receiving member in normal use.

Preferably the rod has a bore for receiving said clevis bolt, to fixedly couple the rod to the clevis ring in use. Suitably the rod can pivot relative to the shaft receiving member and the elongate portion can pivot relative to the rod during adjustment; then, by tightening the clevis bolt, the rod and elongate portion can be held rigidly relative to the shaft receiving member. Suitably the clevis bolt can secure the rod to the shaft receiving member in use, such that the elongate portion can be held between the shaft receiving member and at least part of the rod in use by friction engagement.

Preferably the second component is externally tapered and the cap is correspondingly internally tapered for engagement with the second component in use. The cap and the second component have bores for receiving the bolt in use to secure the cap to the second component in use, such that the tapered engagement is taper-locked firmly to carry substantial torque.

Preferably the prosthesis further comprises a body component, the body component being rotatably coupleable to the shaft in use.

Preferably the shaft has a longitudinal axis, the body component being configured to allow it to rotate relative to the longitudinal axis of the shaft and be retained substantially rigidly at a selected position in normal use.

Preferably the body component is configured to allow it to translate relative to the shaft and be retained substantially rigidly at a selected position in normal use.

Preferably the prosthesis further comprises a third component for attaching to a bone of the subject. Preferably the third component attaches to at least one carpal bone in use. Attachment of a third component to at least one carpal bone is suitable for applications wherein the prosthesis is implanted at a subject's wrist joint. In such applications, the prosthesis comprises a distal radial endo-prosthetic replacement.

In applications where the prosthesis is being used as a mid-radial endo-prosthetic replacement, wherein a mid-section of the radius bone has been resected, the first component will attach to the subject's proximal radial bone remnant, the second component will attach to the subject's ulna and the third component will attach to the subject's distal radial bone remnant. When using the prosthesis as a mid-radial endo-prosthetic replacement, the prosthesis prevents relative movement between the radius and ulna, and prevents the limb from pronating or supinating.

Preferably the prosthesis is configured such that the third component can rotate relative to the longitudinal axis of the first component and can be retained at a selected position in normal use. This allows adjustment of the orientation of the third component relative to the first component before retaining the first and third components substantially rigidly relative to one another for normal use.

Preferably the third component is attachable to the body component in use. Alternatively, the body component may be integral with the third component.

Preferably the third component has a longitudinal axis, the prosthesis being configured such that the longitudinal axis of the third component is non-parallel with the longitudinal axis of the shaft when assembled, the third component being oriented at a fixed angle relative to the longitudinal axis of the shaft when assembled. In other words the third component is not collinear with the shaft when assembled. The fixed angle may be less than 20 degrees. More preferably the fixed angle is between 5 to 15 degrees. Even more preferably the fixed angle is around 10 degrees. The prosthesis is preferably configured such that the third component can rotate relative to the longitudinal axis of the first component and can be retained substantially rigidly at a selected position in normal use.

Preferably the first and second components each comprise a plate for attachment to bone in use.

According to a second aspect of the invention there is provided a prosthesis for implantation at a joint in an animal or human subject, said prosthesis comprising a first proximal component for attaching in use to a first proximal bone of the joint and first distal component for attaching in use to a first distal bone of the joint, the first proximal component and first distal component each having longitudinal axes, the first distal component and first proximal component being coupled together in use such that the longitudinal axis of the first distal component is non-parallel with the longitudinal axis of the first proximal component when assembled, the longitudinal axis of the first distal component being oriented at a fixed angle relative to the longitudinal axis of the first proximal component when assembled.

The prosthesis can provide arthrodesis at the joint, with a fixed angle between the proximal and distal bone(s) of the joint. The prosthesis can be configured to provide a fixed angle between the proximal and distal bone(s) of the joint that is suitable for the particular animal and joint in which the prosthesis is to be implanted.

Preferably the first proximal or first distal component comprises a plate for attachment to bone, the plate being configured for attachment in use to a surface that is on or assembled to the other of the first proximal or first distal component and is sloped at a fixed angle relative to the longitudinal axis of the other of the first proximal or first distal component.

The longitudinal axes of the first distal component and first proximal component are not collinear. Preferably the fixed angle less then 20 degrees. More preferably the fixed angle is between 5 to 15 degrees. Even more preferably the fixed angle is around 10 degrees.

Preferably the prosthesis is configured such that the first distal component can rotate relative to the longitudinal axis of the first proximal component and can be retained substantially rigidly at a selected position in normal use. This allows adjustment of the orientation of the first distal component relative to the first proximal component before retaining the components substantially rigidly relative to one another for normal use.

Preferably the prosthesis further comprises a body component coupleable to the first proximal component and first distal component in use, the body component being configured such that it can rotate relative to the longitudinal axis of the first proximal component or first distal component and can be retained substantially rigidly at a selected position in normal use.

Preferably the prosthesis of the first or second aspects of the invention is for implantation at a carpal joint.

According to a further aspect of the invention there is provided a kit comprising a prosthesis according to the second aspect of the invention, the kit further comprising a plurality of body components, each configured such that the longitudinal axis of the first distal component is oriented at a different angle relative to the longitudinal axis of the first proximal component when assembled. In this way, the surgeon installing the prosthesis can select a body component from a set of body components each configured to give rise to a different fixed angle in the prosthesis when assembled, depending on the particular anatomy of the subject and its joint.

According to a further aspect of the invention there is provided a method of installing a prosthesis, the method comprising the steps of:
  providing a prosthesis according to the first aspect of the invention;
  attaching the first component to a radius bone;
  attaching the second component to an ulna bone;
  rigidly linking the first and second components using said linkage such that the first and second components are retained substantially rigidly relative to one another.

According to a further aspect of the invention there is provided a method of installing a prosthesis, the method comprising the steps of:
  providing a prosthesis according to second aspect of the invention;
  attaching the first proximal component to a first proximal bone;
  attaching the first distal component to an first distal bone;
  coupling the first proximal component and first distal component together in use such that the longitudinal axis of the first distal component is non-parallel with the longitudinal axis of the first proximal component when assembled, the longitudinal axis of the first distal component being oriented at a fixed angle relative to the longitudinal axis of the first proximal component when assembled.

Features mentioned above with respect to the first aspect of the invention may be applied in any combination to the second aspect of the invention, as those skilled in the art will appreciate. Similarly, features mentioned above with respect to the second invention may be applied in any combination to the first aspect of the invention.

The term distal as used herein means located away from the centre of the subject's body when implanted and the term proximal means located near the centre of the subject's body when implanted.

The term subject or patient as used herein refers to a human or animal subject.

BRIEF DESCRIPTION OF THE DRAWINGS

A preferred embodiment of the present invention will now be more particularly described by way of example only with reference to the accompanying drawings, wherein:

FIGS. 1 to 7 show a first embodiment according to the invention;

FIGS. 8 to 11 show a second embodiment according to the invention;

DESCRIPTION OF THE PREFERRED EMBODIMENTS

The present embodiments represent currently the best ways known to the applicant of putting the invention into practice. But they are not the only ways in which this can be achieved. They are illustrated, and they will now be described, by way of example only.

Figure 1:
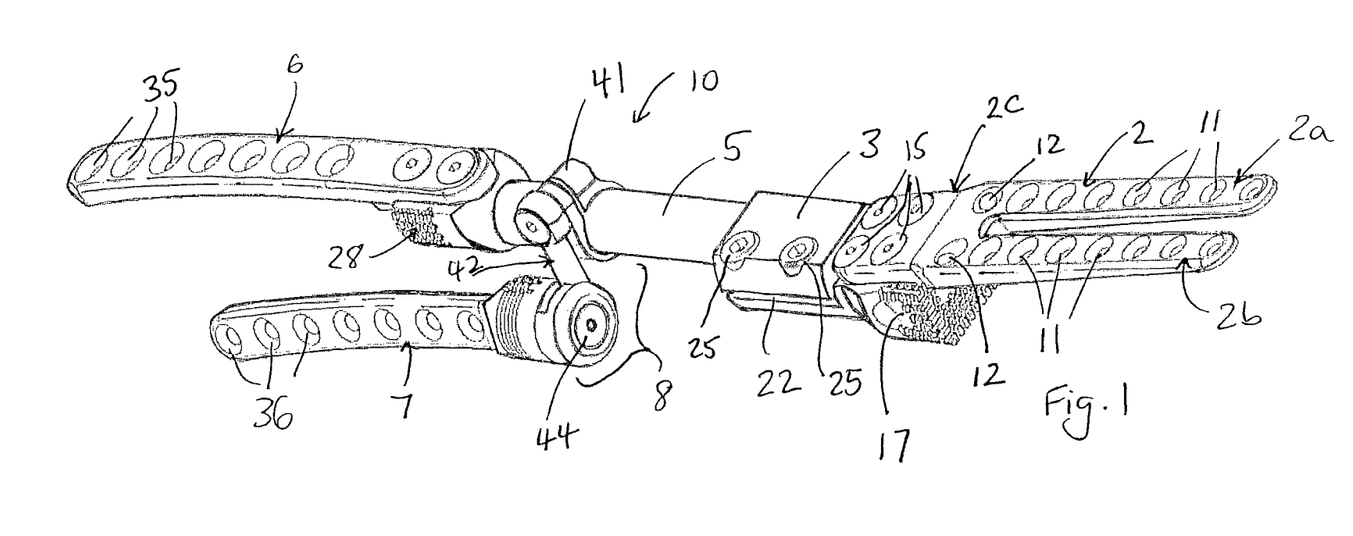
FIG. 1 is a side perspective view of a prosthesis according to the present invention comprising an assembled prosthesis assembly.

Referring to FIG. 1, an endo-prosthetic assembly 10 is shown. The endo-prosthetic assembly 10 is configured for implantation at a joint, in particular a carpal joint (otherwise known as wrist joint) of a human or animal subject. The assembly comprises a first distal plate 2, a body component 3, a shaft 5, a first proximal plate 6, a second proximal plate 7 and a linkage 8, which are shown assembled together in FIG. 1.

Figure 3:
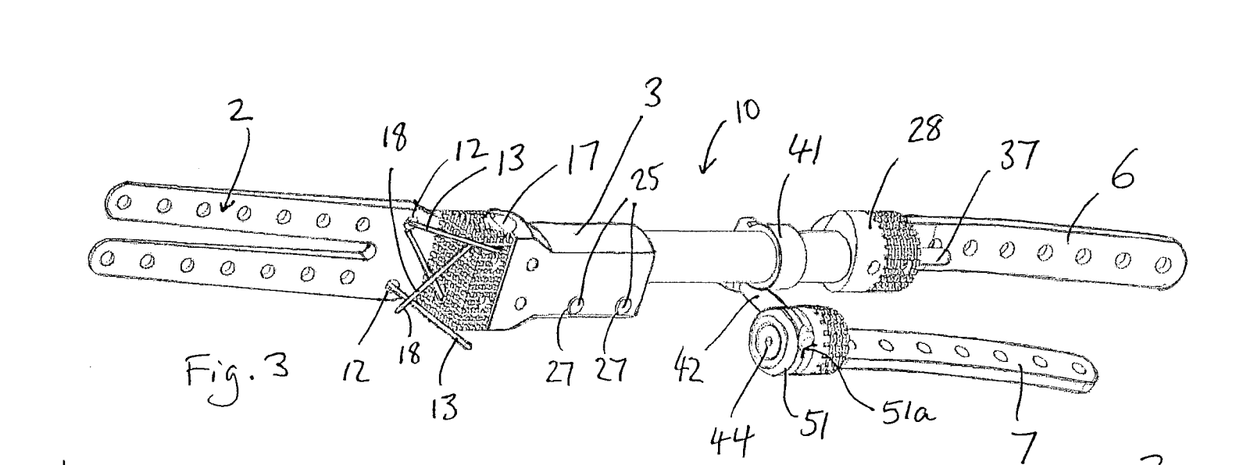
FIG. 3 is an underside perspective view of the prosthesis assembly of FIG. 1.
Figure 4:
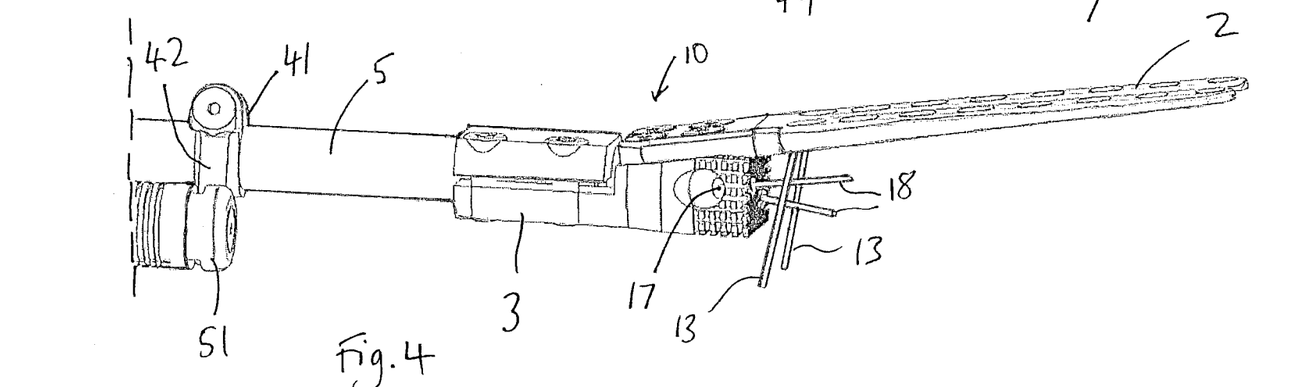
FIG. 4 is a side view of a distal portion of the prosthesis assembly of FIG. 1.

In this embodiment, the first distal plate 2 is adapted for fixation to a bone distal of the joint. When used at the carpal joint, as in this embodiment, the first distal plate 2 is adapted for attachment to carpal bones in use. The distal plate 2 is substantially planar, having a thickness of around 2 to 7 mm. The first distal plate 2 comprises first and second elongate fingers 2a, 2b, rigidly joined at a proximal bridging portion 2c. The first and second fingers 2a, 2b extend substantially parallel with one another and fix to adjacent carpal bones of the wrist in use. The first and second fingers 2a, 2b may fix to the second and third or third and fourth metacarpal bones of the joint respectively. Each of the fingers 2a, 2b has a plurality of holes 11, each for receiving a screw or other suitable fixing, for fixing the finger to bone. The bridging portion 2c also has first and second holes 12, each for receiving a screw or other suitable fixing for fixing the first distal plate 2 to bone. Referring to FIGS. 3 and 4, in this embodiment each of the first and second holes 12 receives a screw 13, the screws 13 extending obliquely to one another for fixation to radial and accessory carpal bones.

The first distal plate 2 may have a hydroxyapatite coated under surface adjacent to the bone when implanted, to aid bone in-growth.

Figure 5:
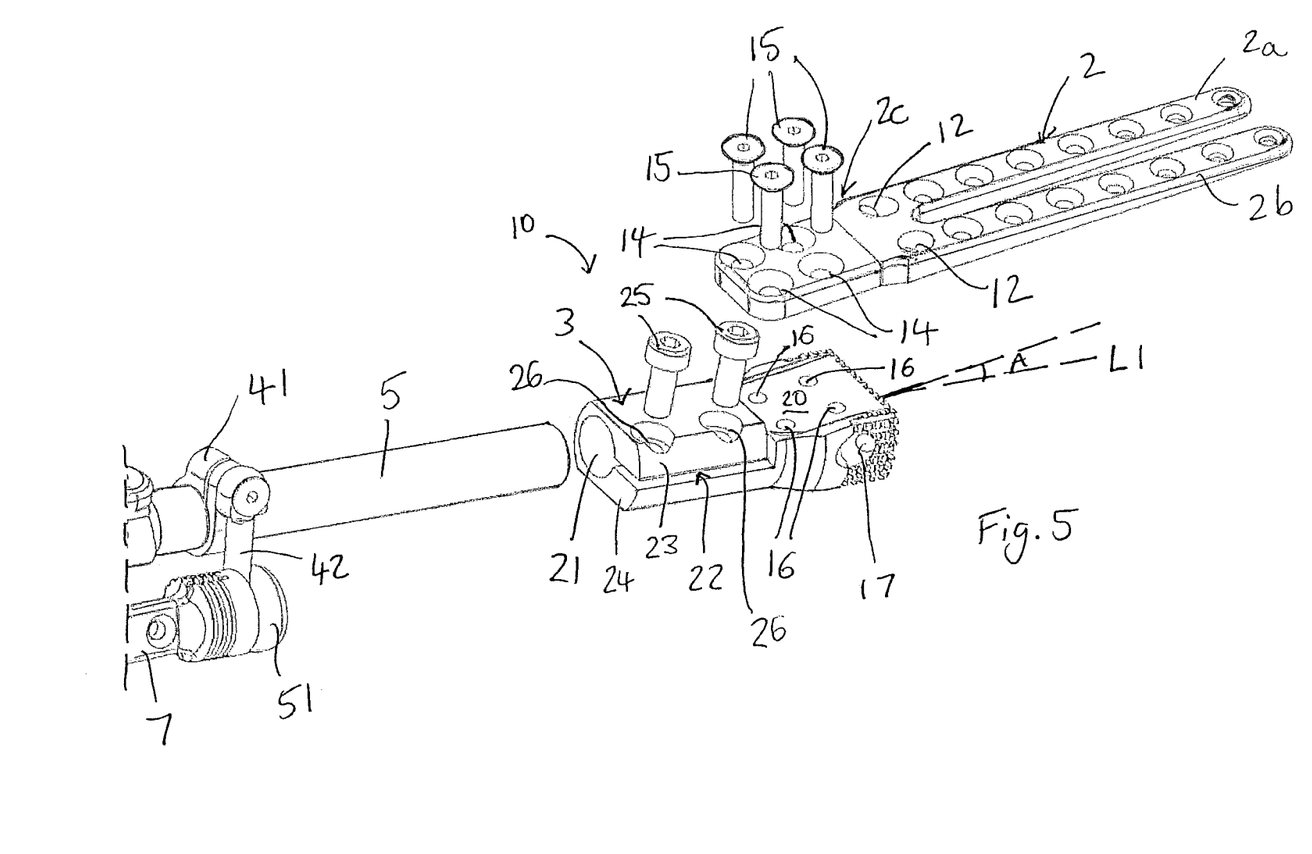
FIG. 5 is a side perspective view of a distal portion of the prosthesis assembly of FIG. 1, shown with the body component and distal plate and associated fixing means exploded from the rest of the assembly.

Referring to FIG. 5, the bridging portion 2c of the first distal plate 2 includes four further holes 14, each for receiving a screw 15. The body component 3 has corresponding holes 16, each for receiving a screw 15, such that the first distal plate 2 can be rigidly secured in use to the body component 3. The body component 3 has two further holes 17, one on the medial side and one on the lateral side of the body component 3 when implanted. The holes 17 have bores that extend obliquely to one another. Referring to FIGS. 3 and 4, holes 17 each receive a screw 18 in use, the screws 18 extending obliquely to one another when inserted in holes 17, towards bone distal of the joint, from the medial and lateral side, to reinforce the interface between the prosthesis assembly and the bone.

The body component 3 may have a hydroxyapatite coated under surface adjacent to the bone when implanted, to aid bone in-growth. In the embodiment of FIGS. 1 to 7, the distal end of the body component 3 is grooved or stippled and may be optionally hydroxyapatite coated to further aid bone in-growth.

Referring to FIG. 5, the body component 3 has a throughbore 21 that extends from the proximal end to the distal end of the component. The throughbore 21 has an open end in the proximal end of the component. The body component 3 has a surface 20 that is sloped relative to the longitudinal axis L1 of the throughbore 21 by a fixed angle A. In this embodiment the fixed angle A is 10 degrees, however the fixed angle A may have other values, preferably being greater than 0 degrees and less than 20 degrees. As explained above, the proximal end of the first distal plate 2 attaches securely and rigidly to the body component 3 in use, by means of screws 15. The distal end of the first distal plate 2 is planar and lies against sloped surface 20 when assembled, such that the longitudinal axis of the first distal plate 2 is offset by angle A relative to the longitudinal axis L1 of the throughbore of body component 3. When the body component 3 and first distal plate 2 are assembled, this provides an angulated 'Y' shaped configuration, wherein the fingers 2a, 2b of the distal plate 2 form the head of the 'Y', which extend at an angle to the stem of the 'Y' formed by the body component 3. Sloped surface 20 is slightly recessed in the body component 3, such that the distal end of the distal plate 2 is constrained by short side walls of the recess, helping to prevent the distal plate 2 from twisting relative to the body component 3 when assembled.

It will be understood that instead of having a first distal plate 2 with first and second fingers for attaching to adjacent carpal bones, the assembly may have separate first and second distal plates for attachment to adjacent carpal bones, each plate being attachable to the body component 3. Furthermore, it is not necessary that the assembly attaches to two bones distal to the assembly when implanted; instead, the assembly may have just a first distal plate that fixes to one distal bone.

The shaft 5 is elongate and assembles between the body part 3 and the first proximal plate 6 in use. The body component 3 has an elongate slot 22 having an elongate axis parallel with throughbore 21, the slot 22 communicating with throughbore 21 and having an elongate opening at one side of the body component 3. The body component 3 has first and second overlapping clamping portions 23,24 above and below the slot, the clamping portions extending perpendicularly away from the longitudinal axis of the throughbore 21. The first clamping portion 23 has two through holes 26 and the second clamping portion 23 has two corresponding through holes 27, for receiving first and second bolts 25 (or other suitable fixing means) for clamping the first and second clamping portions 23, 24 tightly together. In this way, the body component 3 forms a type of clevis ring that can clamp around the shaft by means of bolts 25.

Figure 2:
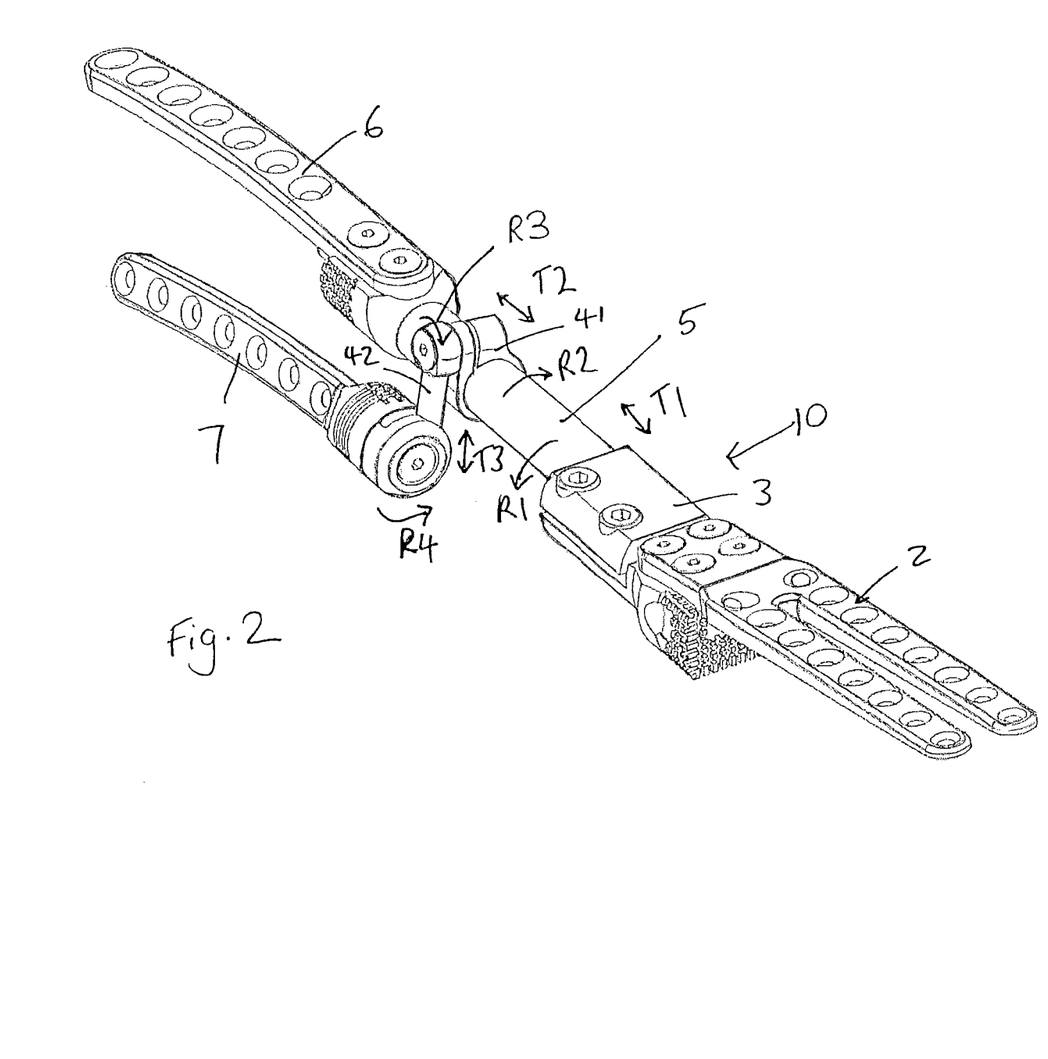
FIG. 2 is a distal end perspective view of the prosthesis assembly of FIG. 1.

When the first and second clamping portions 23, 24 are not clamped tightly together the distal end of shaft 5 can be inserted in the proximal end of the body component 3, and the shaft 5 can be rotated relative to the body component 3 within throughbore 21. This arrangement allows rotational adjustment of the first proximal plate 6 relative to the distal plate 2 and vice versa during implantation, such that the assembly is configured for stable attachment to at least two bones of the subject, irrespective of variations in anatomy between subjects. This allows for pronation/supination adjustment of the distal plate 2 relative to the first proximal plate 6 during implantation to reach the desired orientation between the first proximal plate and first distal plate. Referring to FIG. 2, this arrangement provides a rotational degree of freedom R1 of the shaft 5 (and therefore the first proximal plate 6 to which the shaft 5 is rigidly assembled in use) relative to the body component 3 (and therefore to the distal plate 2, to which the body component is rigidly assembled in use). Once the first and second clamping portions 23, 24 have been clamped tightly together using bolts 25, the distal end of shaft 5 is rigidly held in throughbore 21, and is not able to rotate with respect to body component 3.

Furthermore, when the first and second clamping portions 23, 24 are not clamped tightly together the distal end of shaft 5 can be adjusted back and forth within the body component 3 (i.e. the distal end of shaft 5 can telescope within throughbore 21). The bolted clamp arrangement around shaft 5 allows for adjustment of the overall length of the assembly, and therefore adjustment of the length between the proximal end of first proximal plate 6 and the distal end of distal plate 2 during implantation. Referring to FIG. 2, this arrangement provides a translational degree of freedom T1 of the shaft 5 (and therefore the first proximal plate 6 to which the shaft 5 is rigidly assembled in use) relative to the body component 3 (and therefore to the distal plate 2, to which the body component is rigidly assembled in use). Once the first and second clamping portions 23, 24 have been clamped tightly together using bolts 25, the distal end of shaft 5 is rigidly held in throughbore 21, and is not able to move translationally with respect to body component 3.

Figure 6:
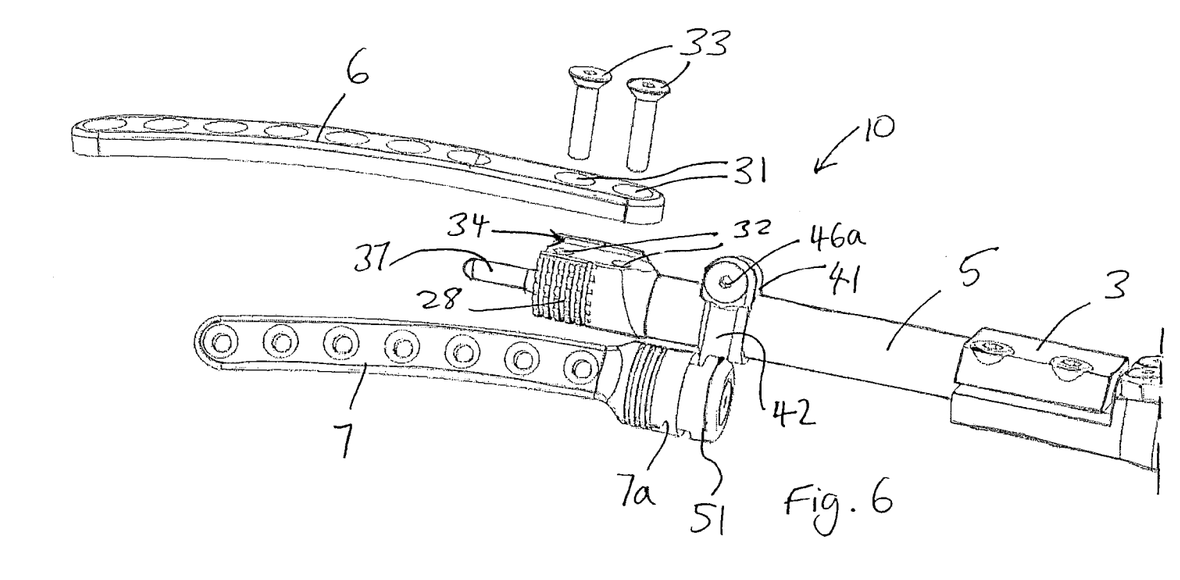
FIG. 6 is a side perspective view of a proximal portion of the prosthesis assembly of FIG. 1, shown with the first proximal plate and associated fixing means exploded from the rest of the assembly.

Referring to FIG. 5, the distal portion of the shaft 5 is cylindrical in shape, such that it is shaped for insertion in throughbore 21. Referring to FIG. 1, the shaft 5 has an enlarged portion 28 at its proximal end. In the embodiment of FIGS. 1 to 7, a curved under surface of enlarged portion 28, which is adjacent bone when implanted, has grooves or stipples coated with hydroxyapatite to aid bone in-growth. Referring to FIG. 6, there is a short intramedullary stem 37 extending from the distal end of the enlarged portion 28, for receipt within an intramedullary cavity of the radius when implanted, to further fix the prosthesis assembly relative to the radius.

Referring to FIG. 1, the first proximal plate 6 is a curved radial plate for attachment to the radius in a wrist joint. In subjects where the distal portion of the radius bone has been resected due to distal radial disease, the first proximal plate 6 will be attached to the proximal radial bone remnant. The first proximal plate 6 is attached in use to the radial bone using bone screws (not shown), receivable through a plurality of holes 35 on plate 6. One or more bone screws can be used to secure the plate 6 to the bone as appropriate. The first proximal plate 6 may have a hydroxyapatite coated under surface adjacent to the bone when implanted, to aid bone in-growth.

Referring to FIG. 6, the distal end of first proximal plate 6 has two holes 31 and the enlarged portion 28 of the shaft has two corresponding holes 32, for receiving bolts 33, to rigidly secure the first proximal plate 6 to the shaft 5. The distal end of first proximal plate 6 seats in use in a recessed area 34 of the enlarged portion 28 of shaft 5 such that the distal end of the first proximal plate 6 is constrained by short side walls of the recess, helping to prevent the first proximal plate 6 from twisting relative to the body shaft 5 when assembled.

Referring to FIG. 1, the second proximal plate 7 is a curved ulna plate for attachment to the ulna. In subjects where the distal portion of the ulna bone has been resected, the first proximal plate 7 will be attached to the proximal ulna bone remnant. The first proximal plate 7 is attached in use to the ulna bone using bone screws (not shown), receivable through a plurality of holes 36 on plate 7. One or more bone screws can be used to secure the plate 7 to the bone as appropriate. The second proximal plate 7 may have a hydroxyapatite coated under surface adjacent to the bone when implanted, to aid bone in-growth.

Figure 7:
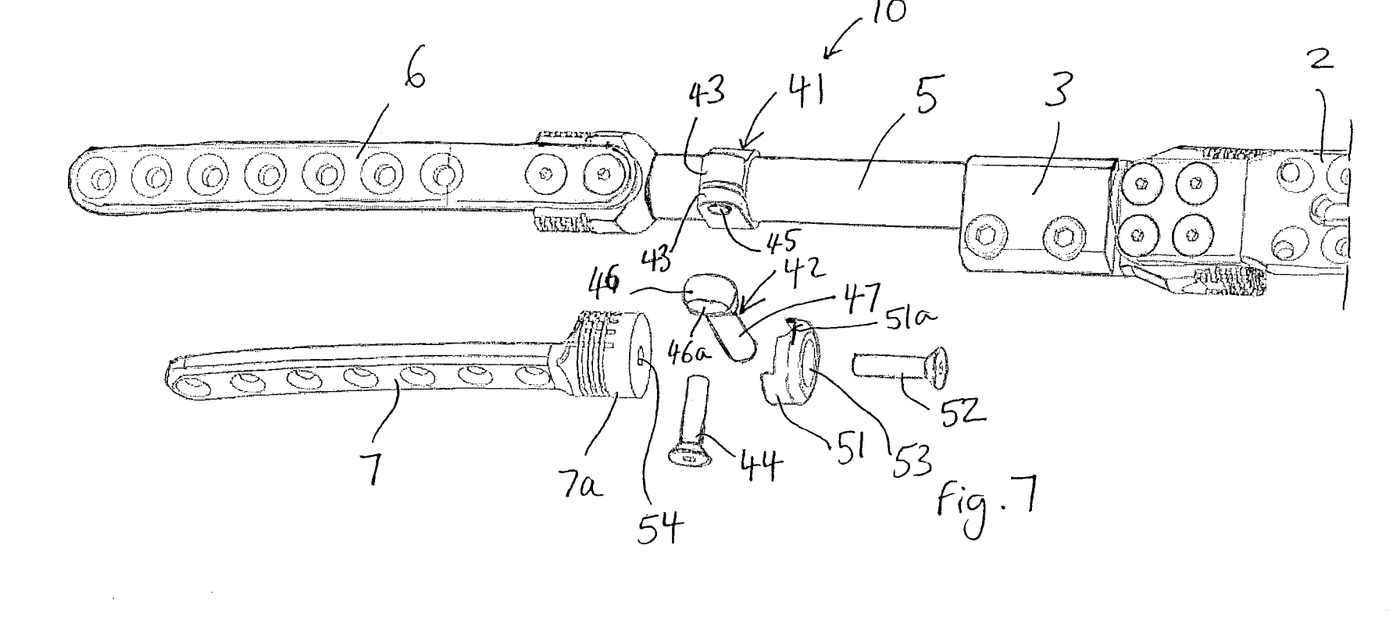
FIG. 7 is a top view of a proximal portion of the prosthesis assembly of FIG. 1, shown with the second proximal plate, coupling member, cap exploded and associated fixing means exploded from the rest of the assembly.
Figure 8:
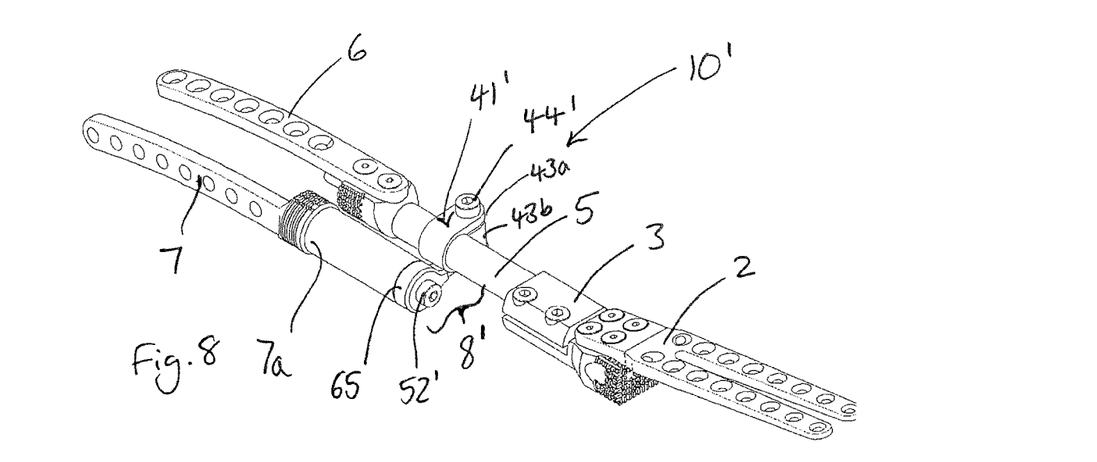
FIG. 8 is a top distal perspective view of an assembled prosthesis assembly according to a second embodiment of the invention.
Figure 9:
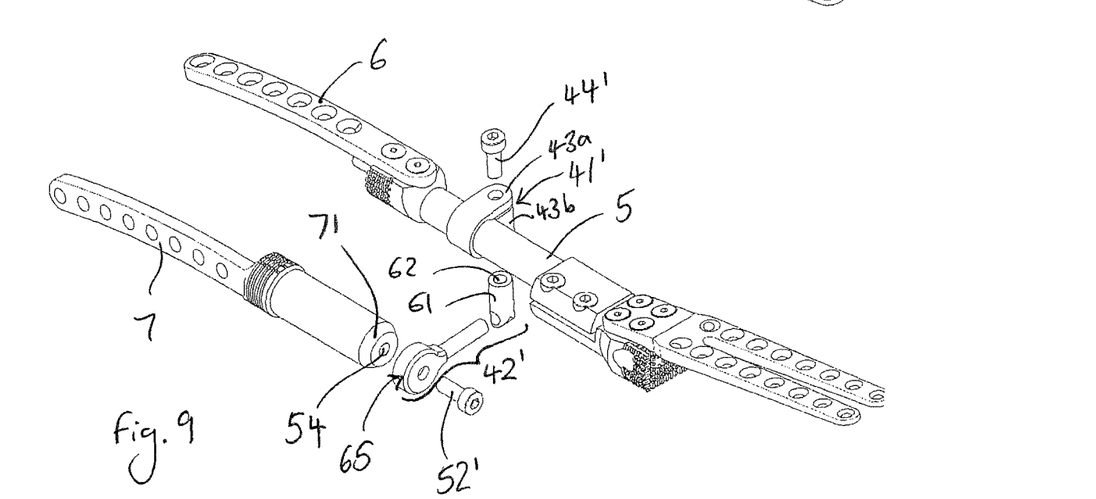
FIG. 9 is a top distal perspective view of the assembly of FIG. 8, showing the linkage and second proximal plate exploded from the rest of the assembly.

Referring to FIG. 7, the second proximal plate 7 has an enlarged distal portion 7a. The enlarged distal portion 7a is substantially cylindrical in shape, having an outer surface that has grooves or stipples coated with hydroxyapatite to aid bone in-growth.

The linkage 8 that links the second proximal plate 7 with the first proximal component 6 (and therefore also with the first distal plate 2) in use will now be described. Referring to FIGS. 1 and 7, the linkage 8 comprises a shaft receiving member 41 and a coupling member 42.

Referring to FIG. 7, the shaft receiving member 41 comprises a clevis ring or the like that clamps around shaft 5. The shaft receiving member 41 has a bore for receiving the shaft 5 therethrough. It also has first and second overlapping ears 43, each having a channel 45 therein for receiving a bolt 44. Bolt 44 is used to tightly engage overlapping ears 43 to one another, thereby tightly clamping the shaft receiving member 41 rigidly to the shaft 5 by a friction engagement.

When the first and second ears 43 are not clamped tightly together the shaft receiving member 41 can move translationally, back and forth along the shaft 5. Referring to FIG. 2, this arrangement provides a translational degree of freedom T2 of the linkage 8 with respect to the shaft 5. When the first and second ears 43 are not clamped tightly together the shaft receiving member 41 can also move rotationally around the shaft. This arrangement provides a rotational degree of freedom R2 of the linkage 8 with respect to the shaft.

When the first and second ears are clamped tightly together, the shaft receiving member 41 is restrained from moving translationally or rotationally relative to the shaft 5.

The coupling member 42 has a head portion 46 and an elongate portion 47. The head portion 46 has a hole 46a therein. When assembled, the bolt 44 passes through the hole 46a in the coupling member 42, and through holes 45 in the shaft receiving member 41, to couple the coupling member 42 to the shaft receiving member 41. The bolt can have external threading (not shown) that corresponds with internal threading that may be within channels 45 in order to secure the bolt 44 within channels 45 and/or internal threading on a washer (not shown). Other suitable means for tightly clamping overlapping ears 43 to one another can of course be used.

When the bolt 44 is not tightly engaging the coupling member 42 against the shaft receiving member 41 (i.e. the coupling member is only loosely held against the shaft receiving member 41 by the bolt 44), the coupling member 42 can pivot about the longitudinal axis of the bolt 44. This arrangement provides a rotational degree of freedom R3 of the coupling member 42 with respect to an axis collinear with the channels 45 in the shaft receiving member 41 (which in this particular embodiment is perpendicular to the longitudinal axis of the shaft 5, but need not be).

Referring to FIG. 7, the prosthesis assembly further includes a cap 51. The cap has a proximal side that faces the distal end of the second proximal plate 7 when assembled. The proximal side of the cap has a groove 51a therein, shaped to receive the cylindrical shaped elongate portion 47 of the coupling member 42. The cap 51 attaches to the distal end of the second proximal plate 7 in use, using screw 52, which passes through a hole 53 in the cap 51 and into a bore 54 in the distal end of the second proximal plate 7. Preferably screw 52 is threaded, the bore 54 being correspondingly internally screw threaded, such that the screw can be threadedly engaged in bore 54. The elongate portion 47 of the coupling member 42 can be rigidly and non-movably engaged with the second proximal plate 7 by means of a friction engagement by the action of the cap 51 and screw 52 clamping the elongate portion 47 of the coupling member 42 against the distal end of the second proximal plate 7.

When the elongate portion 47 of the coupling member 42 is between the distal end of the second proximal plate 7 and the cap 51 but cap 51 is not tightly engaged against the distal end of the second proximal plate 7 (i.e. cap 51 is only loosely engaged), the second proximal plate 7 can move rotationally around the elongate portion 47. This arrangement provides a rotational degree of freedom R4 of the second proximal plate 7 with respect to the linkage 8. When the elongate portion 47 is between the distal end of the second proximal plate 7 and the cap 51 but cap 51 is not tightly engaged against the distal end of the second proximal plate 7, the second proximal plate 7 can also move translationally relative to the coupling member 42. This arrangement provides a transational degree of freedom T3 of the second proximal plate 7 with respect to the linkage 8.

When the cap 51, coupling member 42 and second proximal plate 7 are assembled and the cap is tightly engaged against the distal end of the second proximal plate 7 using screw 52, the second proximal plate 7 is restrained from moving translationally or rotationally relative to the coupling member 42.

As will be understood from the above, the linkage 8 allows for easy adjustment of the bone attachment plates 2, 6, 7 relative to one another, which assists when installing the prosthesis assembly.

In operation, in order to install the assembly, each bone attachment plate 2, 6, 7 may be attached to the corresponding bone, and then the individual parts of the assembly assembled together, using the adjustability of the linkage 8 and the adjustable coupling of the shaft 5 with the coupling body 3 to allow the individual parts of the assembly to couple with one another irrespective of the subject's anatomy.

In a preferred installation method for installation at the wrist, the first proximal plate 6, the second proximal plate 7 and the distal plate 2 are each attached to corresponding bones, then a distal assembly (comprising the distal plate 2 and body component 3) is coupled to a first proximal assembly (comprising the first proximal plate 6 and shaft 5 assembled thereto), then the shaft 5 and second proximal plate 7 are linked together using the linkage 8, as will be described further below. In this preferred installation method, the distal end of the shaft 5 is inserted into the bore of the shaft receiving member 41 to assemble shaft receiving member 41 to the shaft. The shaft 5 is attached to the first proximal plate 6. The first proximal plate 6 is offered to the radius and oriented relative to the bone until it is located on a part of the bone that is optimal for fixation of bone screws thereto. The proximal plate 6 is then fixed to the radius using screws. The second proximal plate 7 is offered to the ulna, and similarly the plate is oriented relative to the bone until it is located on a part of the bone that is suitable for fixation to using bone screws. The distal plate 2 is offered to carpal bones and oriented to a suitable fixation location and fixed thereto using screws. The body component 3 may be attached to the distal plate 2 before or after the distal plate 2 is attached to bone. The shaft 5 is then inserted in the throughbore 21 body component 3. The shaft 5 can translate within the body component to provide a suitable length between the components to link the bone anchored first proximal plate 6 and the bone anchored distal plate 2. The shaft 5 and body component 3 can also be rotated relative to one another to provide the desired rotational orientation between the first proximal plate 6 and distal plate 2. The body component 3 is then rigidly fixed to shaft 5 using bolts 25 so that the shaft 5 and body component 3 can no longer move relative to one another. The linkage 8 is then fully assembled by attaching the coupling member 42 to the shaft receiving member 41 and attaching the coupling member 42 to the distal end of the second proximal plate 7, using one or more of the degrees of freedom T2, T3, R2, R3, R4 as necessary to adjust the linkage 8 before non-movably fixing the shaft receiving member 41 to the shaft 5 and non-movably fixing the coupling member 42 to the shaft receiving member 41 and second proximal plate 7. In this way, the radius and ulna can be linked by virtue of the six degrees of freedom of the assembly, irrespective of the orientation of the bones in the subject.

Alternatively, the prosthesis is assembled, but with each of the couplings each having a degree of freedom T1, T2, T3 R1, R2, R3, R4 as described above being loosely coupled. Each of the bone attachment plates 2, 6, 7 is attached to the corresponding bone and then each of the couplings (i.e. the linkage 8 couplings having degrees of freedom T2, T3, R2, R3, R4 for adjustment of the linkage 8 and the coupling of the shaft 5 with the coupling body 3 having degrees of freedom T1, R1) are tightened such that all parts of the prosthesis assembly are held substantially rigidly with respect to rest of the prosthesis assembly.

Once the assembly is assembled and rigid, the bone attachment plates 2, 6, 7 are fixed with respect to one another so that they cannot move with respect to one another. This causes arthrodesis of the joint. When the prosthesis assembly is fully implanted and made rigid, the distal bones of the joint will be held at a fixed angle A relative to the proximal bones of the joint, due to the extension of the distal plate 2 obliquely relative to the first proximal plate 6.

Once the assembly is assembled and rigid, the linkage 8 provides rigid fixation of the first proximal plate 6 relative to the second proximal plate 7. Where the assembly is implanted at the wrist joint as described in relation to the embodiment of FIGS. 1 to 7, this effectively provides rigid fixation of the radius relative to the ulna, preventing pronation and supination of the limb. The linkage provides such fixation of the radius relative to the ulna irrespective of their orientations by virtue of the multiple degrees of freedom of the linking components using modular connections.

FIGS. 8 to 11 show an alternative embodiment of an endoprosthetic assembly 10' like that shown in FIGS. 1 to 7, except that the embodiment of FIGS. 8 to 11 has a modified linkage 8'. Instead of having a coupling member with elongate portion receivable under a cap that couples to the second proximal plate 7 like the linkage 8 of FIGS. 1 to 7, the modified linkage 8' has a cap with elongate portion that is received within a bore of a rod that couples to the shaft receiving member. Like reference numerals have been used in FIGS. 8 to 11 for those features which are the same as in the embodiment of FIGS. 1 to 7. The modified linkage 8' of the embodiment of FIGS. 8 to 11 will now be described.

The linkage 8' comprises a shaft receiving member 41' and a coupling means or coupling member 42'. Similar to the embodiment of FIGS. 1 to 7, the shaft receiving member 41' comprises a clevis ring or the like that clamps around shaft 5. The shaft receiving member 41' has a bore for receiving the shaft 5 therethrough and first and second overlapping ears 43a and 43b, each having a channel 45a, 45b therein for receiving a bolt 44'. Bolt 44' is used to tightly engage overlapping ears 43a, 43b to one another. When the first and second ears 43a, 43b are not clamped tightly together the shaft receiving member 41' can move translationally, back and forth along and rotationally around the shaft 5. This arrangement provides a translational degree of freedom T2' and a rotational degree of freedom R2' of the linkage 8' with respect to the shaft 5. When the first and second ears 43a, 43b are clamped tightly together, the shaft receiving member 41' is restrained from moving translationally or rotationally relative to the shaft 5.

Figure 10:
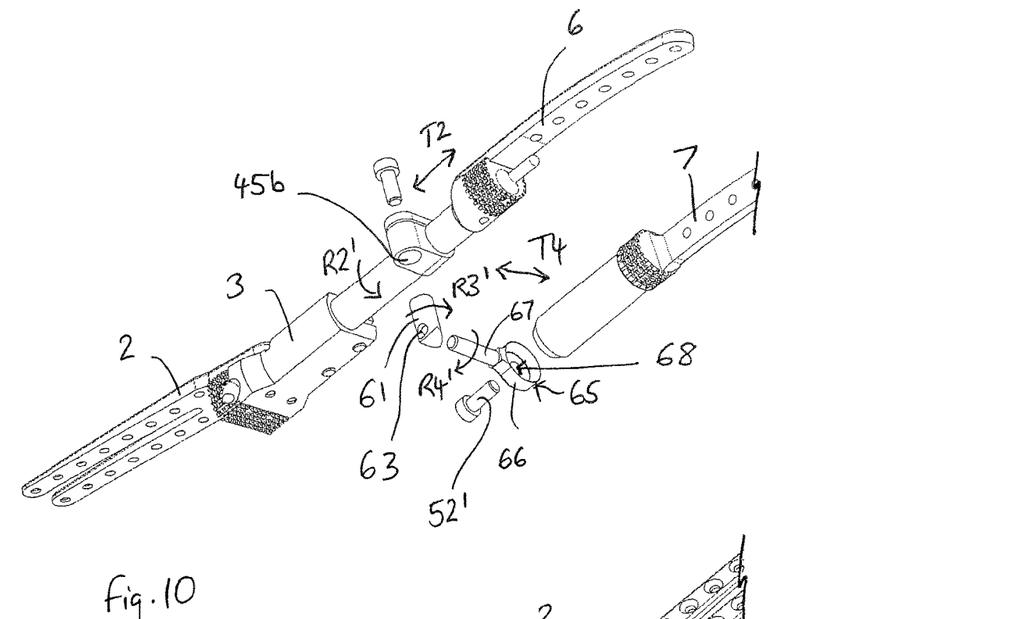
FIG. 10 is an underside perspective view of the exploded assembly of FIG. 9.
Figure 11:
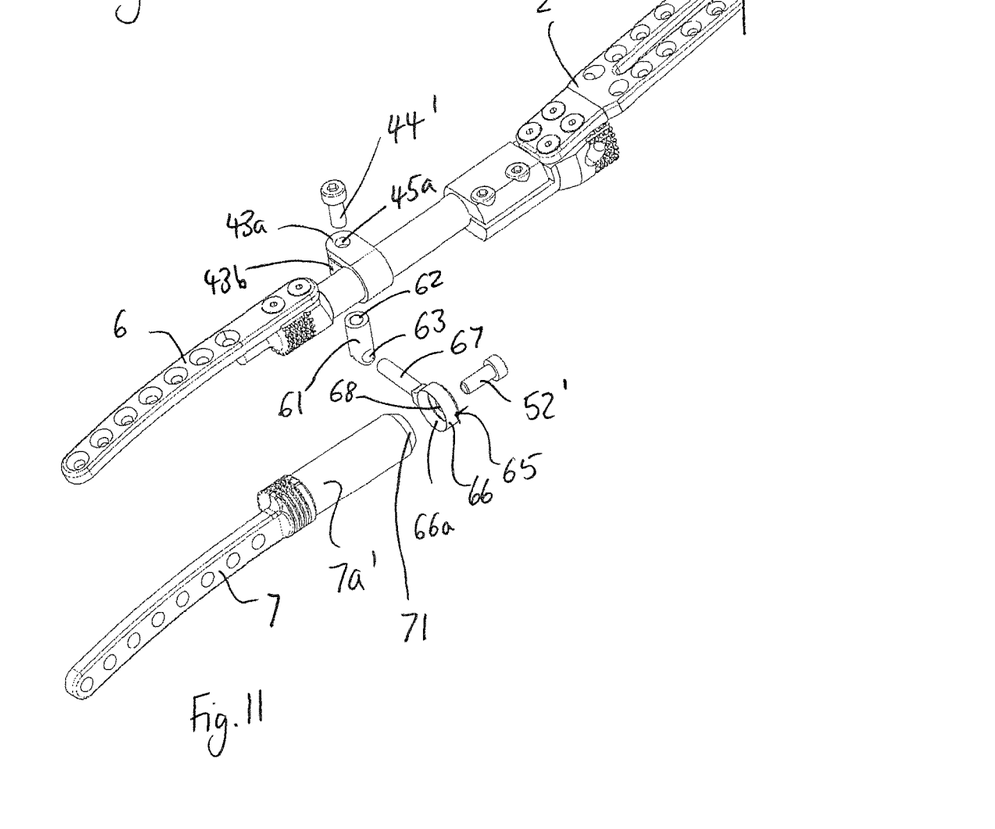
FIG. 11 is a top proximal perspective view of the exploded assembly of FIG. 9.

The coupling member 42' comprises a rod 61 and a cap 65. The rod 61 is a short elongate member, having a first end and a second end, and having an internally threaded channel 62, collinear with a longitudinal axis of the rod 61, and having an opening in the first end. Referring to FIG. 10, the channel 45b of the second overlapping ear 43b of the shaft receiving member 41' is sized to receive the first end of the rod 61. Referring to FIG. 11, the channel 45a of the first overlapping ear 43a and the channel 62 of the rod 61 are both sized to receive the bolt 44'. The bolt 44' has external threading (not visible in the figures), corresponding with the internal threading of channel 62. When assembled, the bolt 44' passes through overlapping ears 43a, 43b and into the channel 62 in rod 61, in order to couple the rod 61 to the shaft receiving member 41'.

Cap 65 has a circular shaped portion 66 has an elongate portion 67 extending therefrom. Rod 61 has a bore 63 in its second end, the bore 63 being sized to receive the elongate portion 67 of the coupling member.

The cap 65 attaches to the distal end of the second proximal plate 7 in use, using screw 52', which passes through a hole 68 in the cap 65 and into a bore 54 in the distal end of the second proximal plate 7. Preferably screw 52' is externally threaded, the bore 54 being correspondingly internally screw threaded, such that the screw can be threadedly engaged in bore 54. The cap 65 can be rigidly and non-movably engaged with the second proximal plate 7 by means of a friction engagement by the action of screw 52' clamping the cap 65 against the distal end of the second proximal plate 7.

When the linkage 8' is assembled, the elongate portion 67 of the cap 65 passes through the bore 63 in the rod 61. When the rod 61 is assembled to the shaft receiving member 41' using bolt 44' as described above, this couples the cap 65 to the shaft receiving member 41'. The elongate portion 67 of the cap 65 can be rigidly and non-movably engaged with respect to the shaft 5 (and therefore the first proximal plate 6 when the shaft 5 is coupled thereto) by means of a friction engagement by the action of the rod 61 clamping the elongate portion 67 received through it up against the shaft receiving member 41', the tight engagement of the elongate portion 67 against the shaft receiving member 41' being secured using the bolt 44'.

When the bolt 44' is not tightly engaging the rod 61 relative to the shaft receiving member 41' (i.e. when the rod 61 of the coupling member is only loosely held relative to the shaft receiving member 41' by bolt 44'), the rod 61 can pivot about the longitudinal axis of the bolt 44'. This arrangement provides a rotational degree of freedom R3' of the rod 61 of the coupling member with respect an axis along the channels 45a,45b in the shaft receiving member (and therefore a rotational degree of freedom R3' of the second proximal plate 7 with respect to the first proximal plate 6). When the linkage 8' is only loosely assembled (i.e. is adjustably assembled), the elongate portion 67 can also pivot relative to rod 61 about the longitudinal axis of the elongate portion 67. This arrangement provides a rotational degree of freedom R4' of the elongate portion 67 relative to the rod 61 and therefore a further rotational degree of freedom of the second proximal plate 7 with respect to linkage 8'. When the linkage 8' is only loosely assembled, the elongate portion 67 can also move translationally relative to the rod 61, back and forth within bore 63. This provides a translational degree of freedom T4 of elongate portion 67 relative to the rod 61 and therefore of the second proximal plate 7 with respect to linkage 8'.

When the cap 65 is tightly engaged with the second proximal plate 7 and the elongate portion 67 of the cap 65 is tightly engaged with the shaft receiving portion 41', the second proximal plate 7 is restrained from moving translationally or rotationally relative to the shaft 5.

The translational and rotational degrees of freedom R2', R3', R4', T2' and T4 of linkage 8' provide the second proximal plate 7 with six degrees of freedom of adjustment relative to the first proximal plate 6 before the components of the linkage 8' are releasably tightened such that all parts of the linkage 8' are held substantially rigidly with respect to the rest of the prosthesis assembly. The prosthesis assembly of FIGS. 8 to 11 can be assembled similarly as described in relation to the prosthesis assembly of FIGS. 1 to 7, in that the assembled linkage 8' can be adjusted via one or more of the degrees of freedom R2', R3', R4', T2' and T4 when the linkage 8' components are loosely coupled, before the linkage 8' components are tightened such that all parts of the prosthesis assembly are held substantially rigidly with respect to one another. The degrees of freedom R2', R3', R4', T2' and T4 of linkage 8' combined with the other degrees of freedom of the prosthesis assembly, R1 and T1, provide for easy adjustment of the prosthesis assembly during installation.

In the embodiment of FIGS. 8 to 11 the distal end 71 of the second proximal plate 7 is conical shaped, providing the distal end with a taper. The cap 65 has a proximal side 66a that faces the distal end 71 of the second proximal plate 7 when assembled. The proximal side 66a has a corresponding internal taper to that of the distal end 71 of the second proximal plate 7 and fits over the tapered distal end 71 when installed. The tapered engagement of the distal end 71 and cap 65 provides an improved frictional engagement of the linkage 8' with the second proximal plate 7 than in the embodiment of FIGS. 1 to 7. The tapered engagement of the cap 65 over the distal end 71 of the second proximal plate 7 provides taper-locking, to prevent the cap 65 from working loose, even if subjected to substantial torque forces. Preferably the taper has a shallow angle of around 20°.

In the embodiment of FIGS. 8 to 11 the second proximal plate 7 has an enlarged distal portion 7a' that is substantially cylindrical in shape, like that of the embodiment of FIGS. 1 to 7, but which is longer than that of the embodiment of FIGS. 1 to 7. The cylindrical enlarged distal portion 7a' of the embodiment of FIGS. 8 to 11 is longer than that of FIGS. 1 to 7 to accommodate situations where a greater length of ulnar bone resection is required. Like the embodiment of FIGS. 1 to 7, the enlarged distal portion 7a' of FIGS. 8 to 11 has a proximal portion having an outer surface that has grooves or stipples coated with hydroxyapatite to aid bone in-growth.

The whole of the prosthesis assembly or some parts of the prosthesis assembly of any of the embodiments described herein may be made of titanium alloy, stainless steel alloy or polyetheretherketone (PEEK), with or without carbon fibres embedded therein.

Each of the bone attachment plates 2, 6, 7, may be attached to intact bone or the remaining portion of a bone after resection of the bone.

It will be understood that instead of having bone attachment plates, the assembly may have other bone fixing means, each fixing means being any suitable means for fixation to bone, such as a bone receiving socket or an intramedullary rod.

The endo-prosthetic assembly 10 or 10' of FIGS. 1 to 11 is particularly suitable for implantation at a carpal joint in a human or animal subject, as described above. However, it will be understood that the assembly could be used at other sites in the human or animal skeleton. For example, the assembly could be used as a mid-radial replacement prosthesis. The assembly could also be modified for installation as a distal tibial replacement assembly for example. In this case, the assembly would have a first distal bone fixing means for attachment to metatarsal bone and a first proximal bone fixing means for attachment to the tibia, the components being held at a fixed angle relative to one another. In this embodiment, a second proximal bone fixing means and linkage 8 would not be needed. In this embodiment, it will be understood that a first proximal component may have a body component integral with it or assembled to it in use, to which a shaft extending from a first distal component in use can rotate and/or translate, for ease of adjustment before rigid fixation of the first proximal component relative to the first distal component.

It will be understood that the prosthesis assembly is a modular assembly. Each part of the assembly can be substituted with a modified part to suit the particular anatomy at the site of implantation. The assembly can be provided as a modular kit in which a range of body components 3 are available, each having a surface 20 sloping at a different angle relative to throughbore 21, to provide for different fixed angle A between the first distal plate 2 and the shaft 5. Furthermore, the assembly can be provided as a modular kit in which a range of lengths and/or shapes for each bone fixation plate 2,6,7 can be provided so that the optimum length/shape plate to suit a particular subject's bone can be selected.

In the prosthesis assemblies of FIGS. 1 to 11, the shaft 5 with enlarged end 28 and the second proximal plate 7 with enlarged distal portion 7a,7a' are each single integral pieces. However, it will be understood that these components, and the other components of the assembly may each comprise two or more parts that assemble together.

The invention claimed is:

1. An arthrodesis prosthesis for implantation in an animal or human subject for preventing pronation or supination at the wrist joint, said prosthesis comprising a first component for attaching to a radius bone in use and a second component for attaching to an ulna bone in use, the prosthesis further comprising a linkage for linking the first and second components with respect to one another in use, wherein the prosthesis is configurable to allow the linkage to move relative to at least one of the first and second components to allow for adjustment of the linkage relative to said at least one of the first and second components to a selected position and is configurable to be retained substantially rigidly at said select position, such that the first and second components can be retained substantially rigidly relative to one another in normal use in a fixed configuration relative to one another, and wherein the linkage includes a locking mechanism capable of rigidly locking the first and second components at a selectable position and the linkage is configurable to allow the linkage to move relative to the at least one of the first and second components to provide at least two degrees of freedom of movement of the first component relative to the second component when adjusting the linkage to said selected position.

2. A prosthesis according to claim 1, wherein the linkage is configurable to allow the linkage to move relative to the at least one of the first and second components to provide at least three degrees of freedom of movement of the first component relative to the second component when adjusting the linkage to said selected position.

3. A prosthesis according to claim 1, wherein the linkage is configurable to allow the linkage to move relative to the at least one of the first and second components to provide at least four degrees of freedom of movement of the first component relative to the second component when adjusting the linkage to said selected position.

4. A prosthesis according to claim 1, wherein the linkage is configurable to allow the linkage to move relative to the at least one of the first and second components to provide at least five degrees of freedom of movement of the first component relative to the second component when adjusting the linkage to said selected position.

5. A prosthesis according to claim 1, the prosthesis further comprising a shaft extending from the first component in use, the linkage being rotatably couplable to the shaft.

6. A prosthesis according to claim 5, wherein the shaft is removably attachable to the first component.

7. A prosthesis according to claim 5, wherein the linkage comprises a shaft receiving member and a coupling member, the shaft receiving member receiving the shaft in use, the coupling member being coupled to the shaft receiving member and the second component in use.

8. A prosthesis according to claim 7, wherein the coupling member is pivotally couplable to the shaft receiving member in use.

9. A prosthesis according to claim 7, wherein the linkage comprises a clevis ring, the clevis ring having a bore for receiving the shaft in use.

10. A prosthesis according to claim 9, wherein the linkage further comprises a clevis bolt, the clevis ring having first and second overlapping ears, said ears having channels therein for receiving said clevis bolt.

11. A prosthesis according to claim 10, wherein said coupling member has a channel for receiving said clevis bolt, to fixedly couple the coupling member to the clevis ring in use.

12. A prosthesis according to claim 7, wherein the coupling member has a longitudinal axis, the prosthesis further comprising fixing means for fixing the coupling member to the second component, the fixing means being configured to allow the second component to rotate relative to the longitudinal axis of the coupling member and be retained substantially rigidly at a selected position in normal use.

13. A prosthesis according to claim 12, wherein the fixing means comprises a bolt and corresponding cap, the cap and the second component having bores for receiving the bolt in use to secure the cap to the second component in use, such that the coupling member can be held between the second component and cap in use by friction engagement.

14. A prosthesis according to claim 7, wherein the coupling member comprises a rod and a cap, the cap having an elongate portion extending therefrom, the rod having a bore for receiving the elongate portion of the cap in use.

15. A prosthesis according to claim 14, wherein the shaft receiving member is configured to receive said rod in use.

16. A prosthesis according to claim 15, wherein the rod has a bore for receiving said clevis bolt, to fixedly couple the rod to the clevis ring in use.

17. A prosthesis according to claim 13, wherein the second component is externally tapered and the cap is correspondingly internally tapered for engagement with the second component in use.

18. A prosthesis according to claim 5, wherein the prosthesis further comprises a body component, the body component being rotatably coupleable to the shaft in use.

19. A prosthesis according to claim 18, wherein the shaft has a longitudinal axis, the body component being configured to allow it to rotate relative to the longitudinal axis of the shaft and be retained substantially rigidly at a selected position in normal use.

20. A prosthesis according to claim 1, wherein the prosthesis further comprises a third component for attaching to a bone of the subject.

21. A prosthesis according to claim 20, wherein the prosthesis is configured such that the third component can rotate relative to a longitudinal axis of the first component and can be retained at a selected position in normal use.

22. A prosthesis according to claim 20, wherein the prosthesis further comprises a body component, the body component being rotatably couplable to the shaft in use and wherein the third component is attachable to the body component in use.

23. A prosthesis according to claim 18, wherein third component has a longitudinal axis, the prosthesis being configured such that the longitudinal axis of the third component is non-parallel with the longitudinal axis of the shaft when assembled, the third component being oriented at a fixed angle relative to the longitudinal axis of the shaft when assembled.

24. A prosthesis according to claim 1, wherein the prosthesis is for implantation at a carpal joint.

25. A method of installing a prosthesis, the method comprising the steps of:
provide a prosthesis according to claim 1;
attaching the first component to a radius bone;
attaching the second component to an ulna bone;
rigidly linking the first and second components using said linkage such that the first and second components are retained substantially rigidly relative to one another.

* * * * *